US00PP32753P2

(12) United States Plant Patent
de Jong

(10) Patent No.: US PP32,753 P2
(45) Date of Patent: Jan. 12, 2021

(54) ***HYPERICUM* PLANT NAMED 'KOLPEKE'**

(50) Latin Name: ***Hypericum* x *inodorum***
Varietal Denomination: Kolpeke

(71) Applicant: KOLSTER HOLDING, B.V., Boskoop (NL)

(72) Inventor: Jan de Jong, Heelsum (NL)

(73) Assignee: KOLSTER HOLDING B.V., Boskoop (NL)

( * ) Notice: Subject to any disclaimer, the term of this patent is extended or adjusted under 35 U.S.C. 154(b) by 0 days.

(21) Appl. No.: 16/602,893

(22) Filed: Dec. 19, 2019

(51) Int. Cl.
*A01H 5/08* (2018.01)
*A01H 6/00* (2018.01)

(52) U.S. Cl.
USPC ..... Plt./442

(58) Field of Classification Search
USPC ..... Plt./442, 226
CPC ... A01H 5/02; A01H 5/00; A01H 5/12; A01H 5/08; A01H 6/00
See application file for complete search history.

(56) References Cited

PUBLICATIONS

Sande Flowers *Hypericum* , retrieved on Jun. 22, 2020, retrieved from the Internet at http://www.sandeflowers.com/pd-31090-1-13916/product/hypericum, 2 pp. (Year: 2020).*

* cited by examiner

*Primary Examiner* — June Hwu
(74) *Attorney, Agent, or Firm* — Penny J. Aguirre

(57) ABSTRACT

A new cultivar of *Hypericum* plant named 'Kolpeke' that is characterized by its leaves that are small in size and healthy, its large sized berries that are light orange-pink in color, and its branches that are held upright.

2 Drawing Sheets

Botanical classification: *Hypericum* x *inodorum*.
Variety denomination: 'Kolpeke'.

BACKGROUND OF THE INVENTION

The present invention relates to a new and distinct cultivar of *Hypericum* x *inodorum* and will be referred to hereafter by its cultivar name, 'Kolpeke'. 'Kolpeke' is a semi-evergreen shrub grown for use as a landscape plant and for container plantings.

The new cultivar was derived from a controlled breeding program conducted by the Inventor in Heelsum, The Netherlands. The overall purpose of the breeding program was to develop new cultivars of *Hypericum* plants with unique berry colors and healthy foliage.

The new cultivar arose from a cross made by the Inventor in Heelsum, The Netherlands in June of 2012 between an unnamed plant from the Inventor's breeding program, accession No. 11148-02, as the female parent and accession No. 11101-11 as the male parent. The Inventor selected 'Kolpeke' as a single unique plant amongst the seedlings that resulted from the above cross in August of 2014.

Asexual propagation of the new cultivar was first accomplished by the Inventor by stem cuttings in August of 2014 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Kolpeke' as a unique cultivar of *Hypericum*.

1. 'Kolpeke' exhibits leaves that are small in size and healthy.
2. 'Kolpeke' exhibits large sized berries that are light orange-pink in color.
3. 'Kolpeke' exhibits branches that are held upright.

The female parent of 'Kolpeke' differs from 'Kolpeke' in having berries that are less orange in color and in being less branched. The male parent of 'Kolpeke', differs from 'Kolpeke' in having berries that are less orange in color and more berries per branch. 'Kolpeke' can be most closely compared to the cultivars 'Coco Casino' (not patented) and 'Coco Yoko' (not patented). 'Coco Casino' and 'Coco Yoko' are both similar to 'Kolpeke' in having leaves that are green in color and branches that are brown-green in color. 'Coco Casino' differs from 'Kolpeke' in having berries that are more pink in color and 'Coco Yoko' differs from 'Kolpeke' in having berries that are more peach in color.

BRIEF DESCRIPTION OF THE DRAWINGS

The accompanying colored photographs illustrate the overall appearance and distinct characteristics of the new *Hypericum*. The plants in the photographs were taken of a plant eight months in age as grown outdoors in a one-gallon container in a greenhouse in Redmond, Wash.

The photograph in FIG. 1 provides a side view of 'Kolpeke' with flower buds.

Figure 1:
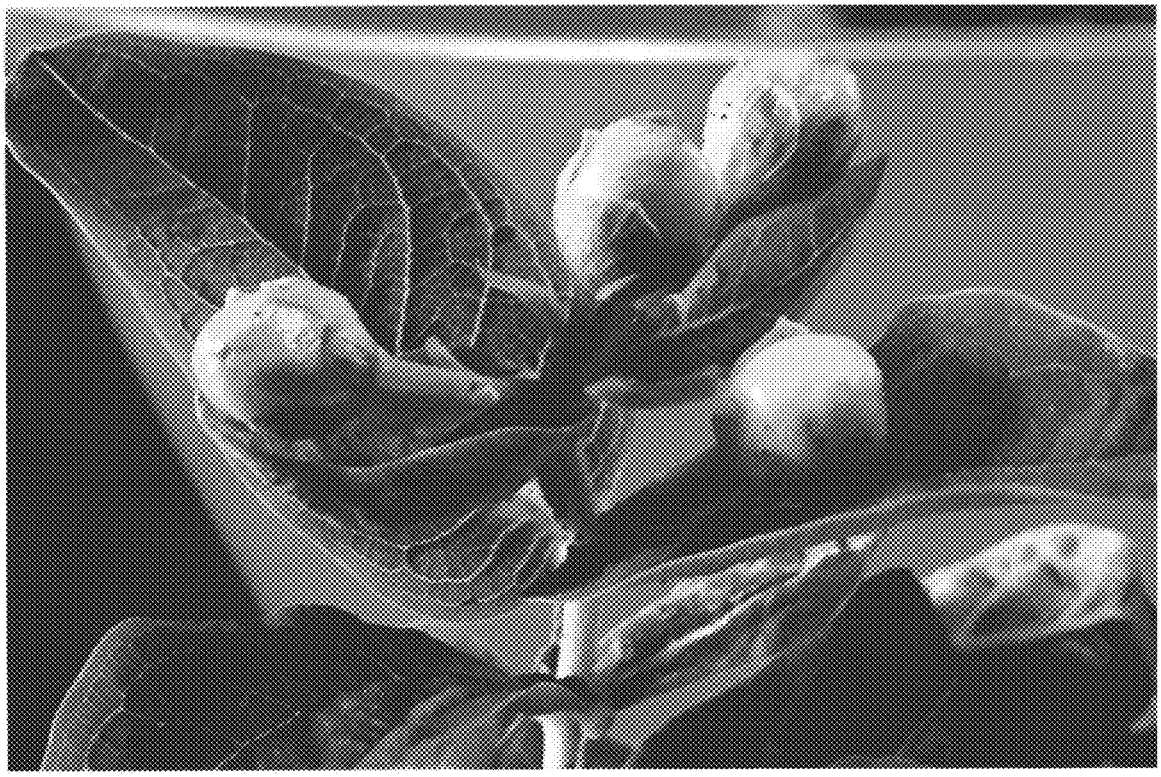
Figure 2:
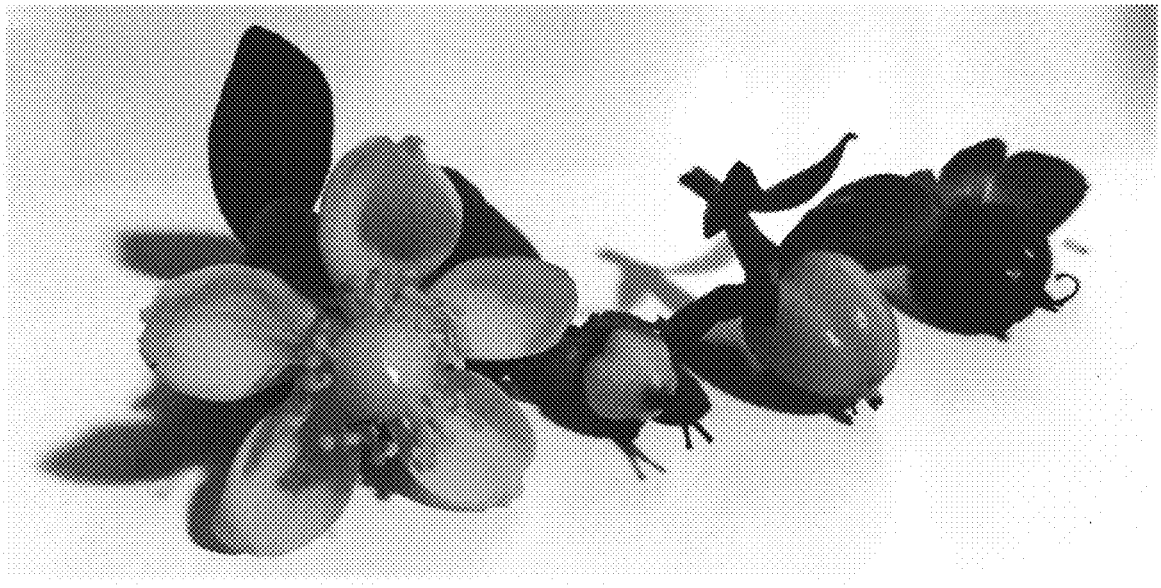

The photograph in FIG. 2 provides a close-up view of a flower and an immature, mature, and aged berries of 'Kolpeke'.

The colors in the photographs are as close as possible with the digital photography techniques available and the color values cited in the detailed botanical description accurately describe the colors of the new *Hypericum*.

DETAILED BOTANICAL DESCRIPTION

The following is a detailed description of eight-month-old plants of the new cultivar as grown in a greenhouse in 1-gallon containers in Redmond, Wash. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—From June to July to September in The Netherlands.

*Plant type.*—Semi-evergreen shrub.

*Plant habit.*—Upright.

*Height and spread.*—Reaches an average of 21 cm in height and 30 cm in spread.

*Cold hardiness.*—Observed to be hardy to at least −20° C.

*Diseases and pests.*—No susceptibility or resistance to diseases or pest has been observed.

*Root description.*—Fibrous and fine, 165A.

*Propagation.*—Vegetative stem cuttings.

*Root development.*—An average of 21 days for root initiation and an average of 35 days to produce a young plant from a rooted cutting.

*Growth rate.*—Moderate.

Stem description:

*Shape.*—Round.

*Stem color.*—New growth; 145A, mature; 199A.

*Stem size.*—Main stems; an average of 19 cm in length and 4 mm in width, lateral branches; an average of 17 cm in length and 2 mm in width.

*Stem surface.*—Glabrous, smooth.

*Internode length.*—Average of 1.5 cm.

*Branching.*—Moderately branched with lateral branches upright to slightly outward held in multiple angles from vertical.

Foliage description:

*Leaf shape.*—Obtuse to elliptic.

*Leaf division.*—Simple.

*Leaf base.*—Cordate to rounded.

*Leaf apex.*—Bluntly acute.

*Leaf fragrance.*—None.

*Leaf venation.*—Pinnate, upper and lower surface color; 145B.

*Leaf margins.*—Entire and undulate.

*Leaf arrangement.*—Opposite.

*Leaf attachment.*—Sessile.

*Leaf substance.*—Moderate.

*Leaf surface.*—Glabrous and dull on upper and lower surface.

*Leaf size.*—An average of 4 cm in length, an average of 3 cm in width.

*Leaf color.*—Young upper and lower surface; 144A, mature upper surface; 147A mature lower surface; 146A.

Inflorescence description:

*Inflorescence type.*—Terminal compound corymb, flat.

*Inflorescence size.*—Average of 6.5 cm in length and 8 cm in width.

*Flower buds.*—Globose to oval in shape with rounded to pointed apex, an average of 5 mm in length and 4 mm in width, 13A in color.

*Flower fragrance.*—None detected.

*Flower quantity.*—An average of 6 per lateral branch.

*Flower type.*—Complete, rotate with reflexed petals and prominent stamens and ovary.

*Flower aspect.*—Upward facing.

*Flower lastingness.*—About 5 days.

*Flower size.*—Average of 2 cm in diameter and 1.5 cm in depth.

*Petals.*—5, elliptic to oblanceolate in shape, un-fused, curved inward, cup-shaped and becoming horizontal, upper surface is glabrous, lower surface glossy, entire margin, truncate base, bluntly acute apex with 1 inward center notch, an average of 1 cm in length and 7 mm in width, when opening and fully open; 9A, maturing to; color upper and lower surface 14A.

*Calyx.*—Reflexed, un-fused sepals, about 1.2 mm in diameter and 3 mm in depth.

*Sepals.*—5, oblong to ovate in shape, an average of 5 mm in length and 7 mm in width, entire margin, round-truncate base, bluntly acute apex, upper and lower surface color; 144A, changing to N144A at the base.

*Peduncles.*—6.5 cm in length and 2 mm in width, 145A in color, glabrous surface.

*Pedicels.*—An average of 1.4 cm in length and 1 mm in width, 145A in color, glabrous surface.

Reproductive organs:

*Gynoecium.*—Pistils; compound, average of 5 mm in length and 1 mm in width, styles; 3, 1A in color and changing to 187A after petal drop, average of 2 mm in length, 0.5 mm in width, glossy surface, stigmas; 3, 1A in color, changing to 187A after petal drop, an average of 1 mm in diameter, round in shape, ovary; superior and 1A in color, after petals drop changing to 155A in color, an average of 5 mm in length and width.

*Androecium.*—Stamens; numerous (an average of 50), spreading outward from base of ovary, 1 cm in length, filaments; 4 mm in length, 0.5 mm in diameter, 15A in color, anthers; 15A in color, club-shaped, an average of 1 mm in length and width, pollen; was not visible.

*Fruit.*—Average of 4 berries per inflorescence, conical in shape with mucronate apex, glabrous and glossy surface; glossiness moderate and lasting into maturity an average of 1 cm in length and 8 mm in width, whitish band at base narrow, cross section triangular, index of apex absent, color; young berry 7C, mature berry 35A, base NN155B, aging berry with a dried raisin like appearance a blend of N186A and 202A.

It is claimed:

1. A new and distinct cultivar of *Hypericum* plant named 'Kolpeke' as herein illustrated and described.

* * * * *